(12) United States Patent
Yokoyama

(10) Patent No.: US 7,914,484 B2
(45) Date of Patent: Mar. 29, 2011

(54) APPLICATOR

(75) Inventor: Kenji Yokoyama, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 12/199,880

(22) Filed: Aug. 28, 2008

(65) Prior Publication Data

US 2009/0005731 A1    Jan. 1, 2009

Related U.S. Application Data

(63) Continuation of application No. PCT/JP2007/053938, filed on Mar. 1, 2007.

(30) Foreign Application Priority Data

Mar. 13, 2006 (JP) .................... 2006-068315

(51) Int. Cl.
    *A61M 37/00* (2006.01)
(52) U.S. Cl. ......................................... 604/83
(58) Field of Classification Search ............ 604/82, 604/289, 296, 140, 83, 191, 119; 222/182, 222/137, 386, 145.5, 327, 391; 239/321, 239/302, 303
    See application file for complete search history.

(56) References Cited

U.S. PATENT DOCUMENTS

| | | | |
|---|---|---|---|
| 5,582,596 A * | 12/1996 | Fukunaga et al. | 604/191 |
| 5,755,362 A | 5/1998 | Rodriguez, Jr. et al. | |
| 6,461,325 B1 * | 10/2002 | Delmotte et al. | 604/82 |
| 6,464,663 B1 | 10/2002 | Zinger | |
| 6,565,539 B1 * | 5/2003 | Zinger et al. | 604/191 |
| 2004/0124217 A1 * | 7/2004 | Yquel et al. | 222/402.21 |
| 2006/0191962 A1 * | 8/2006 | Redl et al. | 222/386 |

FOREIGN PATENT DOCUMENTS

| | | |
|---|---|---|
| JP | 07-100209 A | 4/1995 |
| JP | 09-296039 A | 11/1997 |
| JP | 11-502464 A | 3/1999 |
| JP | 2001-057979 A | 3/2001 |
| JP | 2001-515401 A | 9/2001 |
| JP | 2002-282368 A | 10/2002 |
| JP | 2005-152790 A | 6/2005 |
| WO | WO 95/31138 A1 | 11/1995 |

OTHER PUBLICATIONS

International Preliminary Report on Patentability and Written Opinion (Forms PCT/IB/338, PCT/IB/373 and PCT/ISA/237) issued in corresponding International Patent Application No. PCT/JP2007/053938, Sep. 25, 2008, The International Bureau of WIPO, Geneva, CH.
U.S. Appl. No. 12/068,533, filed Feb. 7, 2008, Yokoyama et al.
U.S. Appl. No. 12/120,041, filed May 13, 2008, Yatabe et al.
U.S. Appl. No. 12/265,498, filed Nov. 5, 2008, Hayakawa.
PCT/ISA/210.

* cited by examiner

*Primary Examiner* — Christopher D Koharski
(74) *Attorney, Agent, or Firm* — Buchanan Ingersoll & Rooney PC

(57) ABSTRACT

An applicator to be used with first and second liquid-containing syringes comprises an applicator main body for receiving the syringes, a gas flow path adapted to be connected to a gas supply for supplying a gas, a nozzle through which is discharged the gas and the liquids in the syringes, an operation part adapted to be pressed to operate pushers of the syringes, and an opening and closing mechanism in the operation part for shutting off/opening the gas flow path. The opening and closing mechanism is operable to open the gas flow path in synchronization with the pressing operation by the operation part.

22 Claims, 7 Drawing Sheets

APPLICATOR

This application is a continuation of International Application No. PCT/JP2007/053938 filed on Mar. 1, 2007, the entire content of which is incorporated herein by reference. This application also claims priority under 35 U.S.C. §119 based on Japanese Application No. 2006-068315 filed on Mar. 13, 2006.

TECHNICAL FIELD

The present invention generally relates to an applicator. More specifically, the invention pertains to a device for mixing together components and delivering, applying or spraying the mixed components to, for example, a region (e.g., diseased region) of a body.

BACKGROUND DISCUSSION

Sprayers have been developed in the past for mixing two or more liquids to form an anti-adhesive material or a living tissue adhesive, and ejecting the mixture to a diseased region of a body.

Such an applicator is configured to separately feed components, which coagulate upon being mixed (such as a thrombin-containing solution and a fibrinogen-containing solution), in a mutually separated manner to the vicinity of the affected part, and to apply them while mixing at the affected part.

One conventional applicator disclosed in Japanese Application publication No. 2001-57979A includes two nozzles (spray heads) respectively connected to opening parts of two syringes respectively containing different types of liquids. The liquids are ejected from the tips of the nozzles and mixed. The applicator described in this application publication is configured as follows in order to mix the two liquids. The respective liquids are ejected together with an aseptic gas so that the respective liquids are ejected in an atomized form. The aseptic gas is fed from a cylinder filled with the aseptic gas connected to a nozzle via a tube. Further, in the cylinder, generally, a closable valve (cock) is set for controlling the supply/stoppage of supply of the gas with respect to the nozzle. When the applicator is used, the valve is previously rendered in an opened state.

However, when the valve is previously rendered in an opened state, unfavorably, the aseptic gas continues being supplied to be involuntarily ejected from the nozzle irrespective of ejection/stop of ejection of the liquid. This causes the following disadvantages: only the aseptic gas continues hitting on the affected part; the aseptic gas is wasted; and other disadvantages. Further, there is another problem as follows: when the applicator is used with the valve rendered in a close state by mistake, respective liquids are ejected without having been atomized, so that the two liquids are applied in an insufficiently mixed state to the affected part.

SUMMARY

An applicator is to be used with a first syringe and a second syringe, with the first syringe and the second syringe each comprising a syringe outer tube having an opening part protruding from a distal end part of the syringe outer tube, a gasket in the syringe outer tube, and a pusher for moving the gasket along a longitudinal direction of the syringe outer tube, and each syringe outer tube being filled with a liquid between the opening part and the gasket. The applicator comprises an applicator main body for receiving the first syringe and the second syringe, a gas flow path adapted to be connected to a gas supply for supplying a gas and through which a gas from the gas supply means passes, and a nozzle through which is discharged the gas which has passed through the gas flow path, the first liquid which has passed though the opening of the first syringe, and the liquid which has passed though the opening part of the second syringe. An operation part is adapted to be pressed to operate the pusher of the first syringe and the pusher of the second syringe in a distal end direction, and an opening and closing means in the operation part shuts off/opens the gas flow path. The opening and closing means is operable to open the gas flow path in synchronization with the pressing operation by the operation part.

When the gas is discharged at a relatively high speed from gas discharge ports in the nozzle, the liquid from the respective syringes that is discharged from respective discharge ports of the nozzle are caught (mixed) in the gas that is discharged from the nozzle. At this step, both the liquids are ejected from the nozzle in an atomized form, and as a result, are mixed with good reliability.

The applicator has useful application to administer a biological tissue adhesive (e.g., an adhesive which, as known, can be applied for example to a cut on the skin or a sutured area). In such a case, one of the two liquids can be a liquid (solution or the like) containing thrombin, and the other can be a liquid (solution or the like) containing fibrinogen. Alternatively, as another example, the applicator has useful application to administer an adhesion preventive material (e.g., a material which, as known, can be applied for example during an operation/medical procedure to prevent adhesion between organs). In such a case, one of the two liquids can be a liquid (solution or the like) containing carboxymethyl dextrin modified with a succinimidyl group, and the other can be a liquid (solution or the like) containing disodium hydrogenphosphate.

In the applicator disclosed here, it is preferable that the two liquids have different liquid compositions, are mixed with each other, and serve as an adhesion preventive material of a biological tissue.

The two liquids gelate (solidify) upon mixing. The gelated two liquids can remain at the biological tissue (objective site) on which they have been applied with good reliability. Further, at the objective site, the mixed composition reliably functions as an adhesion preventive material at the objective site of the living body.

DETAILED DESCRIPTION

Figure 6:
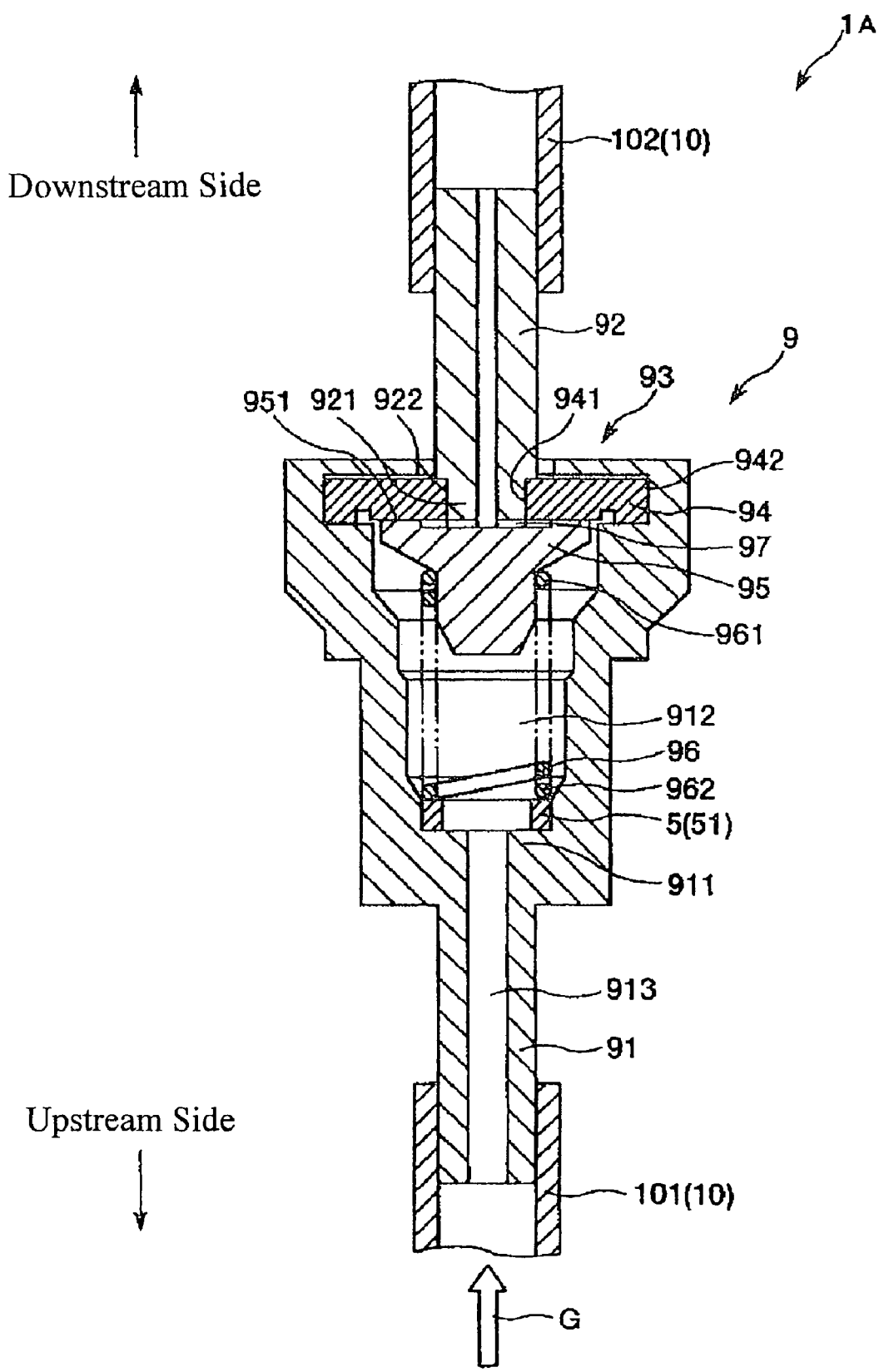
FIG. 6 is a longitudinal cross-sectional view of a second embodiment of the opening and closing means in an applicator.
Figure 7:
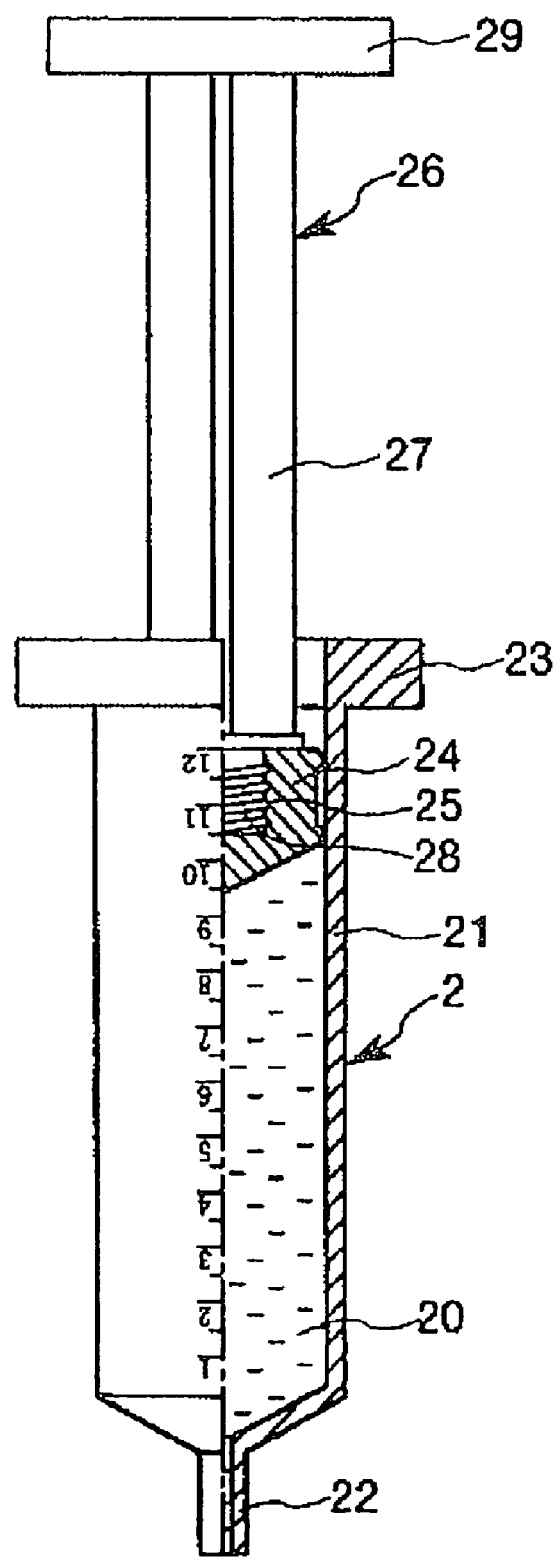
FIG. 7 is a partial longitudinal cross-sectional view of a first syringe to be mounted in the applicator shown in FIG. 1, it being noted that the second syringe possesses a similar construction.

FIGS. 1-7 illustrate various aspects of the applicator disclosed herein. For convenience in description, the left hand side in FIGS. 1, 2 and 5A to 5E is referred to as the "distal end", and the right hand side in FIGS. 1, 2 and 5A to 5E is referred to as the "rear end (proximal end)". In FIG. 7, the lower side is referred to as the "distal end" and the upper side is referred to as the "rear end". Further, in FIGS. 1 to 4, the upper side is referred to as the "top" while the lower side is referred to as the "bottom".

Figure 1:
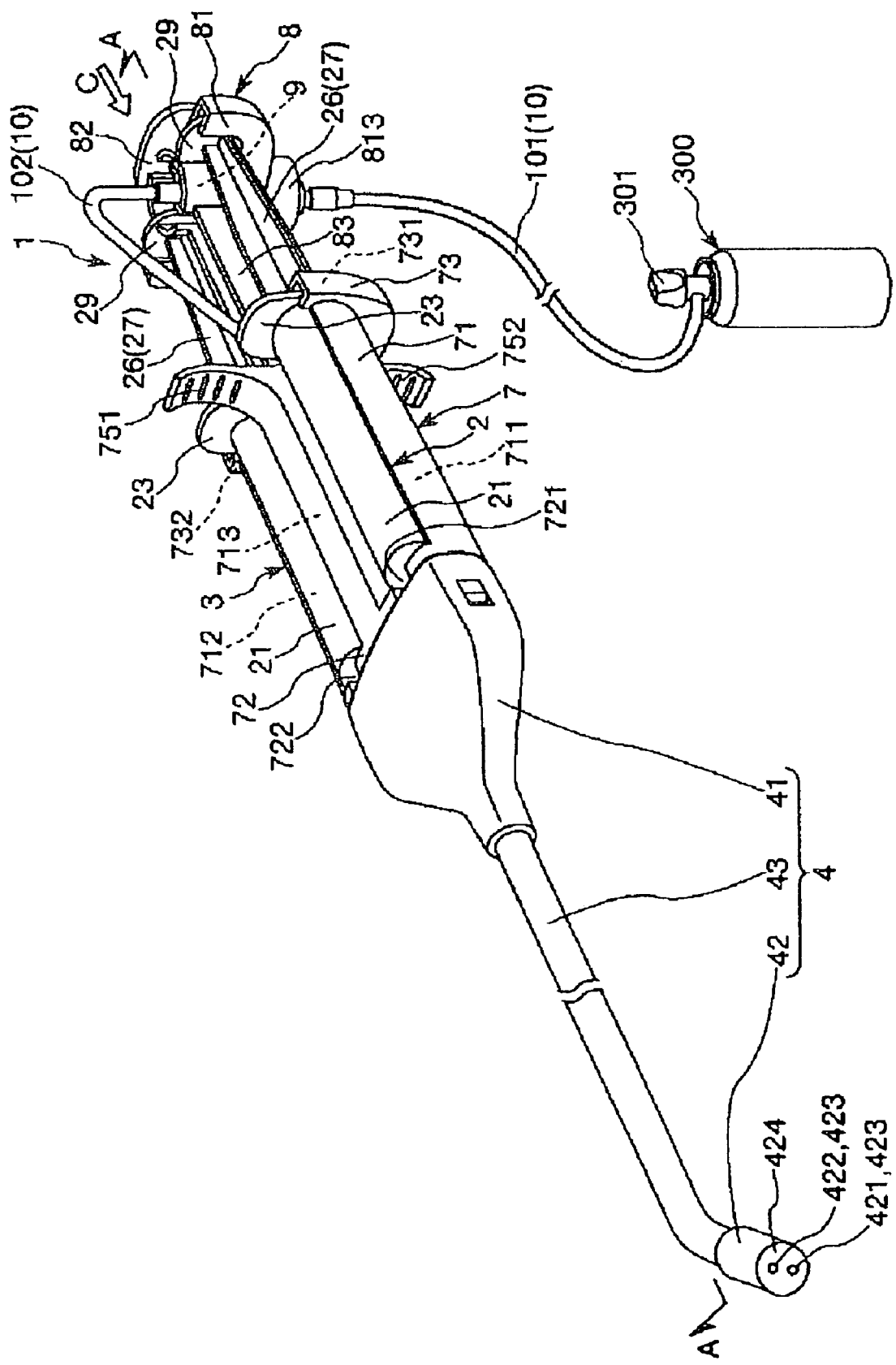
FIG. 1 is a front perspective view of a first embodiment of an applicator disclosed here.
Figure 2:
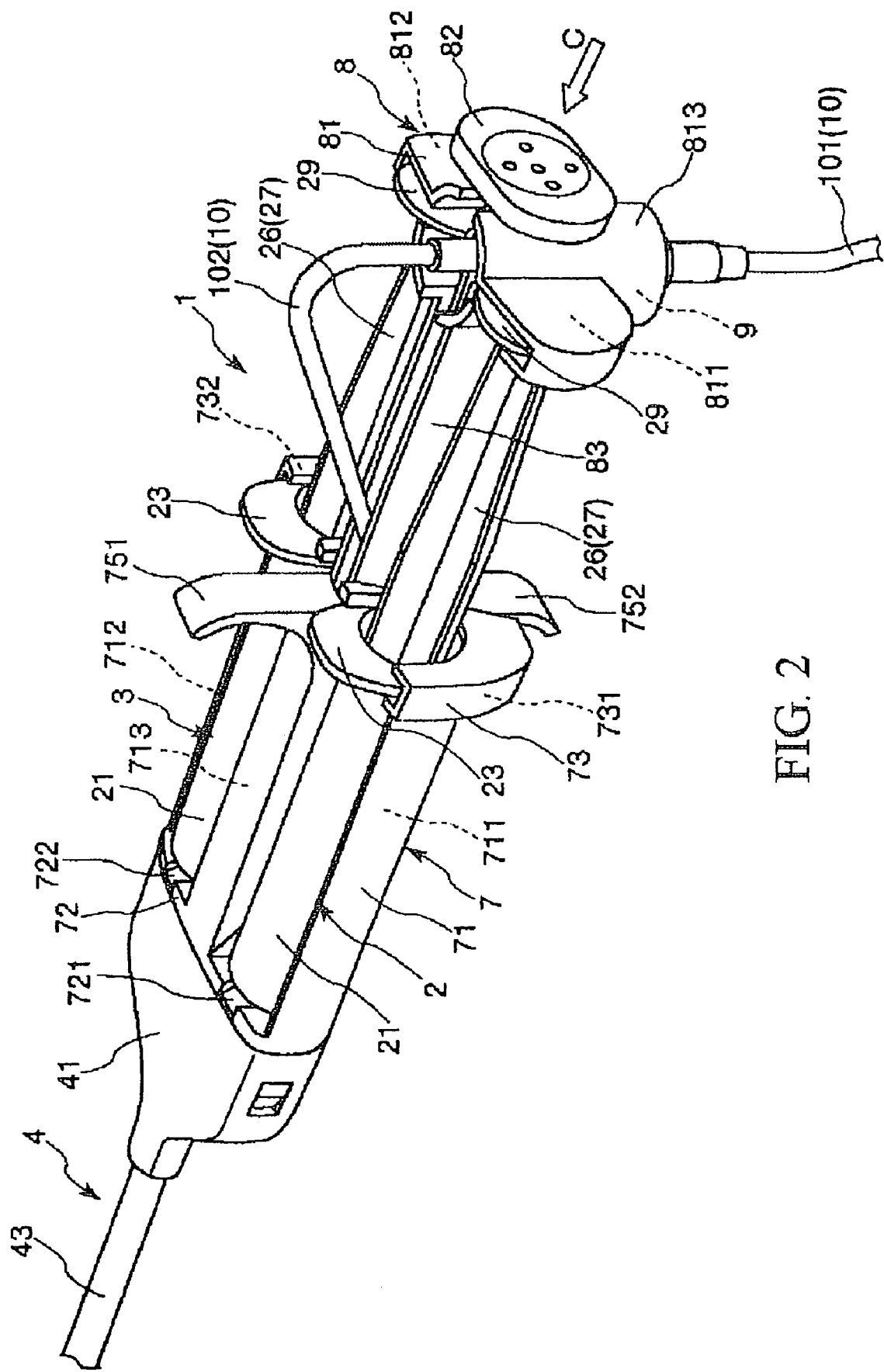
FIG. 2 is a rear perspective view of the first embodiment of the applicator.

As shown in FIGS. 1 and 2, the applicator 1 disclosed here is adapted to be used with a first syringe 2 and a second syringe 3, both of which are mounted in the applicator. The first syringe 2 and the second syringe 3 are roughly the same in configuration. Thus, it is to be understood that the following description of the first syringe 2 applies also to the second syringe 3.

The first syringe 2 is shown in FIG. 7. In this illustrated embodiment, the first syringe 2 includes an outer tube (syringe outer tube) 21, a gasket 24 slidable inside the outer tube 21, and a pusher (plunger rod) 26 for moving and operating the gasket 24 in the longitudinal direction (axial direction) of the outer tube 21. The gasket 24 is connected to the distal end of the pusher 26.

The outer tube 21 is formed of a bottomed tubular member. A reduced diameter part (opening part) 22 is located at the central part of the bottom on the distal end side of the tubular member. The reduced diameter part (opening part) 22 is reduced in diameter with respect to the body of the outer tube 21 and protrudes in the forward or distal direction. The reduced diameter part 22 is integrally formed in one piece with the remainder of the tubular member.

A flange 23 is formed around the periphery of the rear end of the outer tube 21. The flange 23 is integrally formed in one piece with the remainder of the tubular member. A scale indicative of the amount of liquid is provided on the outer circumferential surface of the outer tube 21.

Examples of materials which can be used to form the outer tube 21 include various resins including polyvinyl chloride, polyethylene, polypropylene, cyclic polyolefin, polystyrene, poly-(4-methylpenetene-1), polycarbonate, acrylic resin, acrylnitrile-butadiene-styrene copolymer, polyesters such as polyethylene terephthalate and polyethylene naphthalate, butadiene-styrene copolymer, and polyamide (e.g., nylon 6, nylon 6.6, nylon 6.10, or nylon 12). Out of these, resins such as polypropylene, cyclic polyolefin, and polyesters are preferred in terms of ease of molding and low water vapor permeability. It is preferable that the material forming the outer tube 21 is substantially transparent in order to ensure the visibility of the inside.

The gasket 24 is stored or positioned in the outer tube 21. The gasket 24 formed of an elastic material. A plurality of ring-like projections extend circumferentially around the entire circumference or outer periphery of the gasket 24. In the illustrated embodiment, the gasket is provided with two of such projections. The projections slide while being in close contact with the inner circumferential surface of the outer tube 21. As a result, the fluid tightness is reliably maintained, and the slidability is improved.

A hollow part 25 opening toward the rear end side is formed in the gasket 24. The head part 28 of the pusher 26 is screwed into (engaged with) the hollow part 25. The inner surface of the hollow part 25 is provided with a screw thread (female screw thread).

The material forming the gasket 24 is not particularly limited. Examples of suitable materials are elastic materials including various rubber materials such as natural rubber, butyl rubber, isoprene rubber, butadiene rubber, styrene-butadiene rubber, and silicone rubber, various thermoplastic elastomers of polyurethane type, polyester type, polyamide type, olefin type, styrene type, and other types, or mixtures thereof.

The pusher 26 has a rod-like main body part 27 possessing a cross-shaped cross section. A head part (connecting part) 28 is provided at the distal end side of the main body part 27. The head part (connecting part) 28 is inserted into or positioned in the hollow part 25 of the gasket 24 so that the gasket 24 and the pusher 26 are connected to one another. A screw thread (male screw) is provided around the periphery of the head part 28. This screw thread threadably engages the screw thread of the hollow part 25 of the gasket 24. By screwing the male screw into the female screw, the gasket 24 and the pusher 26 are connected. The connection between the gasket 24 and the pusher 26 is not limited to this threaded engagement. The gasket 24 and the pusher 26 may be configured to be connected by, for example, a concavo-convex fitting, may be configured to be attached by adhesion, fusion, or the like, or may be configured to be integrally formed as a single one-piece unit.

A disk-like flange 29 is formed on the rear end side of the main body part 27 of the pusher 26. The material forming the pusher 26 can be the same ones as those mentioned by way of example above in the description of the outer tube 21.

The first syringe 2 is filled with a first liquid L1 in a space (liquid storage space) 20 surrounded by the outer tube 21 and limited by the gasket 24 before being mounted in the applicator 1.

As with the first syringe 2, the second syringe 3 is also formed of the outer tube 21, the gasket 24 capable of sliding in the outer tube 21, and the pusher 26 for moving and operating the gasket 24. The space 20 is filled with a second liquid L2. The configuration of each of these parts of the syringe is the same as described above and so the description is not again repeated.

The first liquid L1 in the first syringe 2 and the second liquid L2 in the second syringe 3 are different in composition (components) from each other.

The first liquid L1 and the second liquid L2 are appropriately selected according to the use of the applicator 1, the intended purpose, the situation to be addressed, etc. For example, when the applicator is to be used to administer a biological tissue adhesive, one of the two liquids L1, L2 can be a liquid (solution or the like) containing thrombin, and the other can be a liquid (solution or the like) containing fibrinogen.

Alternatively, when the applicator is to be used for administration of an adhesion preventive material, one of the first liquid L1 and the second liquid L2 can be a liquid (solution or the like) containing carboxymethyl dextrin modified with a succinimidyl group, and the other can be a liquid (solution or the like) containing disodium hydrogenphosphate.

The combination of the first liquid L1 and the second liquid L2 gels or starts to solidify upon mixing. The gelation enables, for example, the mixture of the first liquid L1 and the second liquid L2 (hereinafter referred to as a "mixture") to remain at the biological tissue (objective site) at which it is applied with relative reliability. Further, the mixture remains at the objective site with relative reliability. Therefore, the mixture can function as a biological tissue adhesive or an adhesion preventive material at the objective site with relative reliability.

The types and combinations of the first liquid L1 and the second liquid L2 are not limited to the foregoing examples. Other combinations of liquids (materials) may be employed.

The first syringe 2 filled with the first liquid L1 and the second syringe 3 filled with the second liquid L2 are mounted on the applicator. The applicator includes an applicator main body 7, a nozzle 4, an operation part 8, an opening and closing means (valve mechanism) 9, and a tube 10 connected to a gas supply 300 which, in the illustrated embodiment, is a cylinder containing gas (gas supply means) as shown in FIG. 1.

Before describing various parts forming the applicator 1, the gas supply 300 in the form of the cylinder will be described.

The cylinder 300 is filled with a high pressure (compressed) aseptic gas G (which is hereinafter simply referred as a "gas G"). The cylinder 300 can supply the gas G to the applicator 1, specifically the nozzle 4 of the applicator. A closable valve 301 (cock) is applied to the cylinder 300. The closable valve 301 controls the supply of the gas G to the applicator 1 by either permitting or preventing the flow of the gas. When the applicator 1 is in a state of use, the valve 301 is in an open state.

As shown in FIGS. 1 and 2, the applicator main body 7 is configured to permit the first syringe 2 and the second syringe 3 to be positioned in side by side relation (in parallel). The applicator main body 7 includes a base 71, a front plate (first fitting part) 72 at the distal end of the base 71, a rear plate (second fitting part) 73 provided at the rear end of the base 71, and finger rest parts 751, 752 in the vicinity of the rear plate 73 of the base 71.

The upper part of the base 71 includes concave parts or recesses 711, 712 possessing a semi-circular arc in cross section. The concave parts 711, 712 are positioned parallel to one another. The outer tube 21 of the first syringe 2 is stored in the recess or concave part 711 of the base 71 while the outer tube 21 of the second syringe 3 is stored in the recess or concave part 712 of the base 71. Thus, the recess 711 is a first syringe receiving region and the recess 712 is a second syringe receiving region.

The front plate 72 is provided at the distal end of the base 71. The front plate 72 is outfitted with grooves 721, 722 at positions respectively corresponding to the concave parts 711, 712. When the first syringe 2 and the second syringe 3 are mounted in their respective concave parts, the reduced diameter part 22 of the first syringe 2 is positioned in the groove 721, and the reduced diameter part 22 of the second syringe 3 is positioned in the groove 722.

The rear plate 73 is provided at the rear end of the base 71. The rear plate 73 is provided with grooved or concave parts 731, 732 at positions respectively corresponding to the concave parts 711, 712. When the first syringe 2 and the second syringe 3 are mounted in their respective concave parts, the flange 23 (the proximal end part) of the first syringe 2 is fitted (inserted) into the grooved part 731, and the flange 23 (proximal end part) of the second syringe 3 is fitted into the grooved part 732.

Thus, in the applicator main body 7, each reduced diameter part 22 is fitted into the front plate 72, and each flange 23 is fitted into the rear plate 73. As a result, it is possible to fix the first syringe 2 and the second syringe 3 in parallel with reliability.

The finger rest parts 751 and 752 are provided in the vicinity of the rear plate 73 of the base 71. A user using the applicator is able to rest his/her fingers on the finger rest parts 751, 752. The finger rest part 751 is formed of an upwardly protruding plate piece, and the finger rest part 752 is formed of a downwardly protruding plate piece. Further, the respective finger rest parts 751, 752 are configured such that the sides facing the distal end direction each form a circular arc (curved concave shape).

The applicator main body 7 may be configured such that respective parts forming the applicator main body 7 are integrally formed, or it may be configured such that respective parts are respectively formed of separate bodies, and are bonded together.

The material forming the applicator main body 7 is not limited to a particular material. For example, various metal materials, various plastics, and the like may be used alone, or in combination. When such a material is used, the applicator main body 7 can be manufactured with relative ease by, for example, injection molding.

The operation part 8 is positioned at the rear end side of the applicator main body 7. The operation part 8 is adapted to be moved in the longitudinal direction with respect to the applicator main body 7. The operation part 8 is a site for pressing and operating the pusher 26 of the first syringe 2 and the pusher 26 of the second syringe 3 in the direction of the distal end (in the direction of the arrow C in FIGS. 1, 2, and 4). The operation parts 8 has a connection part 81 for connecting the flanges 29 of the pushers 26 of the first syringe 2 and the second syringe 3, a pressing part 82 situated on the rear end side of the connection part 81, and a rail part 83 extending from the connection part 81 toward the direction of the distal end.

The connection part 81 is provided with upwardly opening concave parts or groove regions 811, 812. The concave part 811 possesses a shape corresponding to the flange 29 of the pusher 26 of the first syringe 2, in which the flange 29 is fitted (see FIG. 2). On the other hand, the concave part 812 possesses a shape corresponding to the flange 29 of the pusher 26 of the second syringe 3, in which the flange 29 is fitted (see FIG. 2).

With the connection part 81 having such a configuration, it is possible to connect and fix the flanges 29 of the pushers 26 of the first syringe 2 and the second syringe 3 with quite good reliability. As a result, it is possible to move these pushers 26 integrally at the same time in the direction of the arrow C.

The connection part 81 also includes a tubular part 813 between the concave part 811 and the concave part 812. The tubular part 813 is oriented so that its axis is parallel with the vertical direction in FIG. 1 (as well as FIG. 2). Further, most of the opening and closing means 9 is stored in the tubular part 813.

A long-shaped (elongated) rail part 83 extends from the outer circumferential part of the tubular part 813 of the connection part 81. The elongated rail part 83 protrudes toward the direction of the distal end. The rail part 83 is provided at the base 71 of the applicator main body 7, and extends into an elongated concave or recessed part 713. The pressing operation of the operation part 8 in the direction of the arrow C by the operator (user) guides the rail part 83 into the concave part 713. As a result, it is possible to carry out the pressing operation quite smoothly.

The plate-shaped pressing part 82 is set on the rear end side of the tubular part 813 of the connection part 81. The plate-shaped pressing part 82 is movable in the longitudinal direction of the applicator main body 7 with respect to the tubular part 813.

The pressing part 82 is a part that is to be pressed by a user when the applicator 1 is used, i.e., when the mixture is to be applied onto the affected part or the like. When the applicator 1 is used, for example, an index finger can be rested on the finger rest part 751, a middle finger can be rested on the finger rest part 752, and a thumb can be rested on or press on the pressing part 82. As a result, it is possible to grasp the applicator 1 with good stability and with reliability. Further, it is possible to carry out the pressing operation of the operation part 8 (pressing part 82) with relative smoothness and reliability. This results in an improvement of the operability of the applicator 1.

The pressing part 82 is connected to a second connection part 92 of the opening and closing means described later.

The constituent material of the operation part 8 is not limited to a specific material. Examples of suitable materials include those materials mentioned in connection with the applicator main body 7. When such a material is used, the operation part 8 can be manufactured by, for example, injection molding, with relative ease.

The nozzle 4 is set at the front plate 72 of the applicator main body 7. The nozzle 4 is provided as the part through which is discharged the gas G (gas) which has passed through the tube 10, the first liquid L1 which has passed through the reduced diameter part 22 of the first syringe 2, and the second liquid L2 which has passed through the reduced diameter part 22 of the second syringe 3 (see FIGS. 5A-5E). As shown in FIG. 1, the nozzle 4 includes a nozzle main body 41, a nozzle head 42 situated on the distal end side of the nozzle main body 41, and a connection part 43 connecting the nozzle main body 41 and the nozzle head 42.

The nozzle main body 41 is in the shape of a block and can be formed of, for example, a metal material or a resin material. The reduced diameter part 22 of the first syringe 2 and the reduced diameter part 22 of the second syringe 3, and the tube 10 are fitted and connected to the nozzle main body 41 in a fluid-tight (air-tight) manner.

As shown in FIGS. 1 and 5A-5E, the nozzle head 42 is cylindrical in outer shape. The nozzle head 42 has, in a distal end wall part 424, a first discharge port 421 through which the first liquid L1 is discharged, a second discharge port 422 through which is discharged the second liquid L2, and a pair of third discharge ports (gas discharge ports) 423 through which is discharged the gas G. The first discharge port 421 and the second discharge port 422 are positioned adjacent to each other. Further, in this embodiment, the first discharge port 421 and the second discharge port 422 are equal to each other in size. Respective third discharge ports 423 are positioned around the outer circumferential parts of the first discharge port 421 and the second discharge port 422 roughly concentrically, respectively.

The constituent material of the nozzle head 42 has no particular restriction. For example, the same ones as the constituent material of the nozzle main body 41 can be used.

As shown in FIG. 1, the connection part 43 is an elongated connection part. It connects the distal end of the nozzle main body 41 and the proximal end of the nozzle head 42. The connection part 43 may be either formed of a hard material or formed of a soft material, an elastic material, or the like, and having flexibility. Examples of the constituent material of the connection part 43 may include: various soft and hard resins including polyvinyl chloride, polyethylene, polypropylene, cyclic polyolefin, polystyrene, poly-(4-methylpentene-1), polycarbonate, acrylic resin, acrylnitrile-butadiene-styrene copolymer, polyesters such as polyethylene terephthalate and polyethylene naphthalate, butadiene-styrene copolymer, and polyamide (e.g., nylon 6, nylon 6.6, nylon 6.10, or nylon 12), various rubber materials such as natural rubber, butyl rubber, isoprene rubber, butadiene rubber, styrene-butadiene rubber, and silicone rubber, various thermoplastic elastomers of polyurethane type, polyester type, polyamide type, olefin type, styrene type, and other types, various metal materials such as stainless steel, aluminum, copper, or copper type alloys, and various ceramics such as various glasses, alumina, and silica.

The nozzle 4 is provided with a first flow path 44, a second flow path 45, and a third flow path 46 which penetrate through the nozzle main body 41, the connection part 43, and the nozzle head 42 and extend along the axis (the longitudinal direction) of the connection part 43. The first flow path 44 communicates with the first discharge port 421. Thus, the first flow path 44 can feed the first liquid L1 which has passed through the reduced diameter part 22 of the first syringe 2 into the first discharge port 421. The second flow path 45 communicates with the second discharge port 422. Thus, the second flow path 45 can feed the second liquid L2 which has passed through the reduced diameter part 22 of the second syringe 3 into the second discharge port 422. The third flow path 46 communicates with the third discharge ports 423. Thus, the third flow path 46 can feed the gas G which has been supplied from the cylinder 300 and has passed through the tube 10 to the third discharge ports 423.

With this configuration of the nozzle 4, the gas G is discharged at relatively high speed from each of the third discharge ports 423. The first liquid L1 discharged from the first discharge port 421 and the second liquid L2 discharged from the second discharge port 422 are caught (mixed) into the gas G discharged at high speed. The first liquid L1 and the second liquid L2 are thus each discharged in an atomized form. As a result, the first liquid L1 and the second liquid L2 are mixed with relative reliability, and applied onto the affected part.

The tube 10 is connected to the nozzle 4. The tube 10 functions as a gas flow path through which the gas G supplied from the cylinder 300 passes. Further, the tube 10 is formed of a first tube 101 situated on the upstream side (on the side of the cylinder 300) via the opening and closing means 9, and a second tube 102 situated on the downstream side (on the side of the nozzle 4).

The material forming the tube 10 (the first tube 101 and the second tube 102) is not particularly limited. Examples of materials may include: polyolefins such as polyethylene, polypropylene, and ethylene-vinyl acetate copolymer, polyvinyl chloride, polybutadiene, polyamide, and polyester. Out of these, particularly, polybutadiene is preferably used. Use of polybutadiene for the material forming the tube 10 results in an appropriate flexibility, and excellent chemical resistance, and chemical adsorption preventive property.

As described above, the opening and closing means 9 is set in the tubular part 813 of the operation part 8. The opening and closing means 9 is adapted to permit and prevent the gas G from flowing from the cylinder 300 to the nozzle 4. The first tube 101 and the second tube 102 are alternatively and selectively shut off (see FIG. 3) and communicated with each other (see FIG. 4) by the operation of the opening and closing means 9 through the opening and closing means 9.

Figure 3:
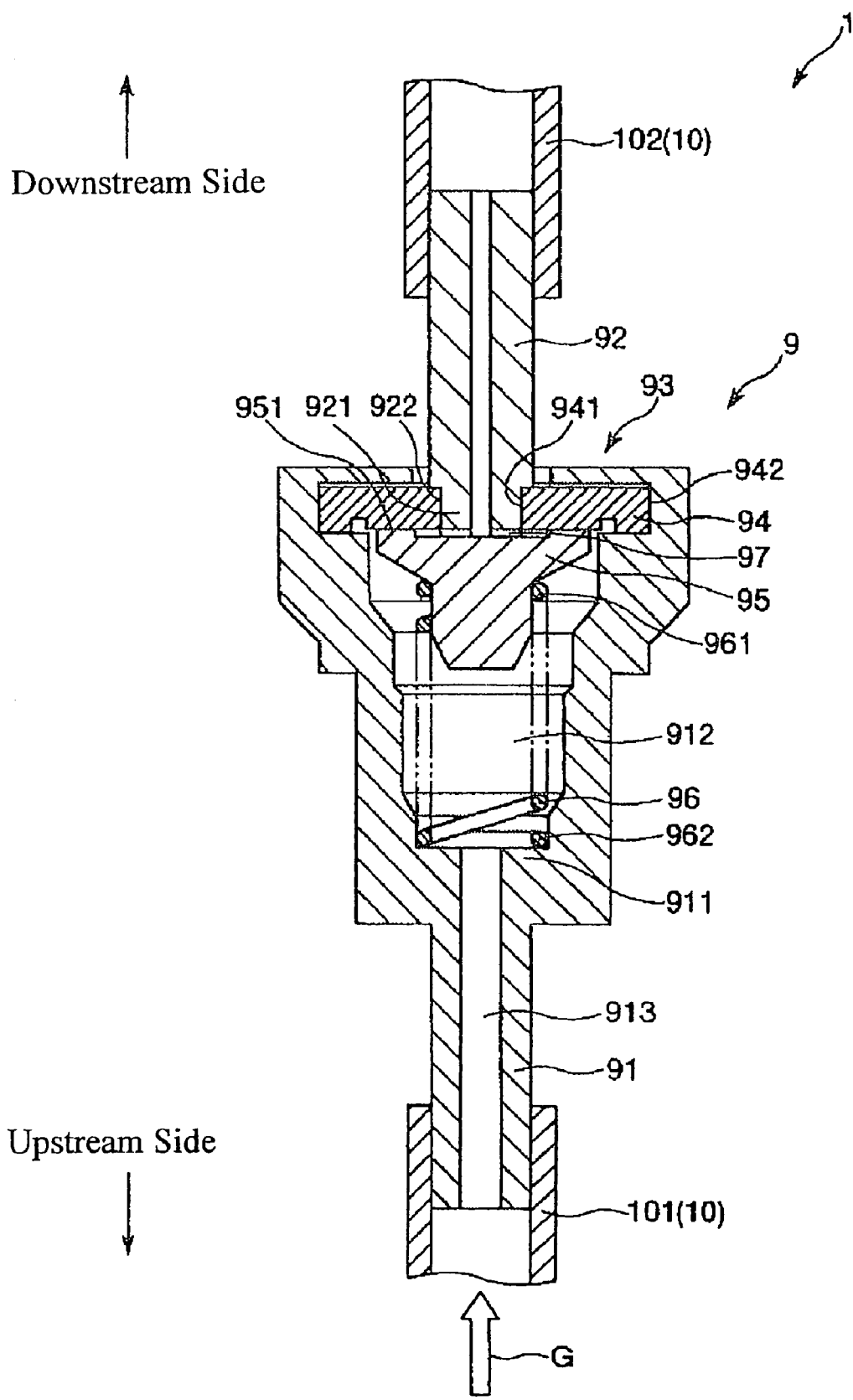
FIG. 3 is a cross-sectional view of the applicator taken along the section line III-III in FIG. 1 illustrating an opening and closing means in a state in which a gas flow path is shut off.
Figure 4:
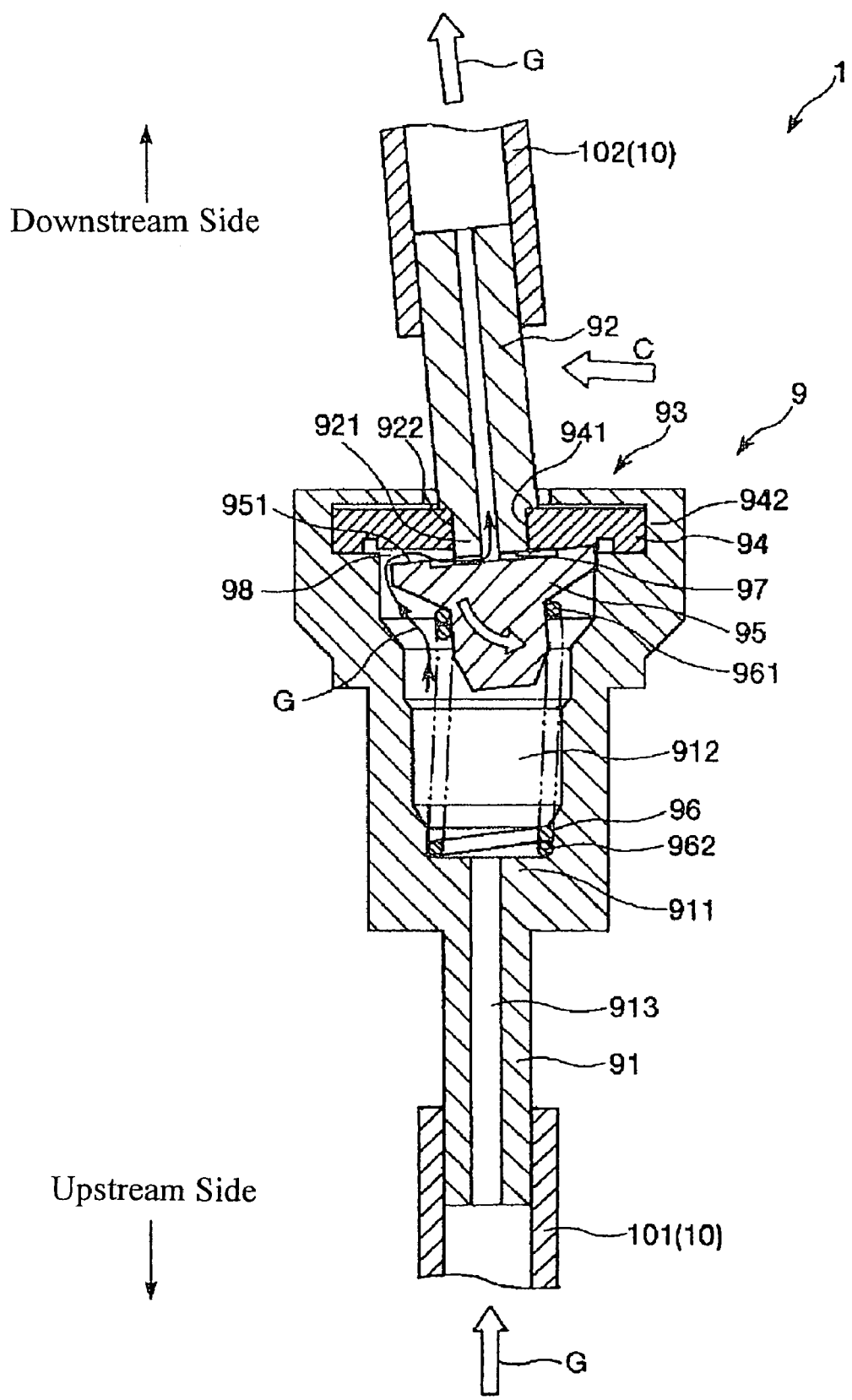
FIG. 4 is a cross-sectional view of the applicator taken along the section line III-III in FIG. 1 illustrating an opening and closing means in a state in which a gas flow path is shut opened.
Figure 5:
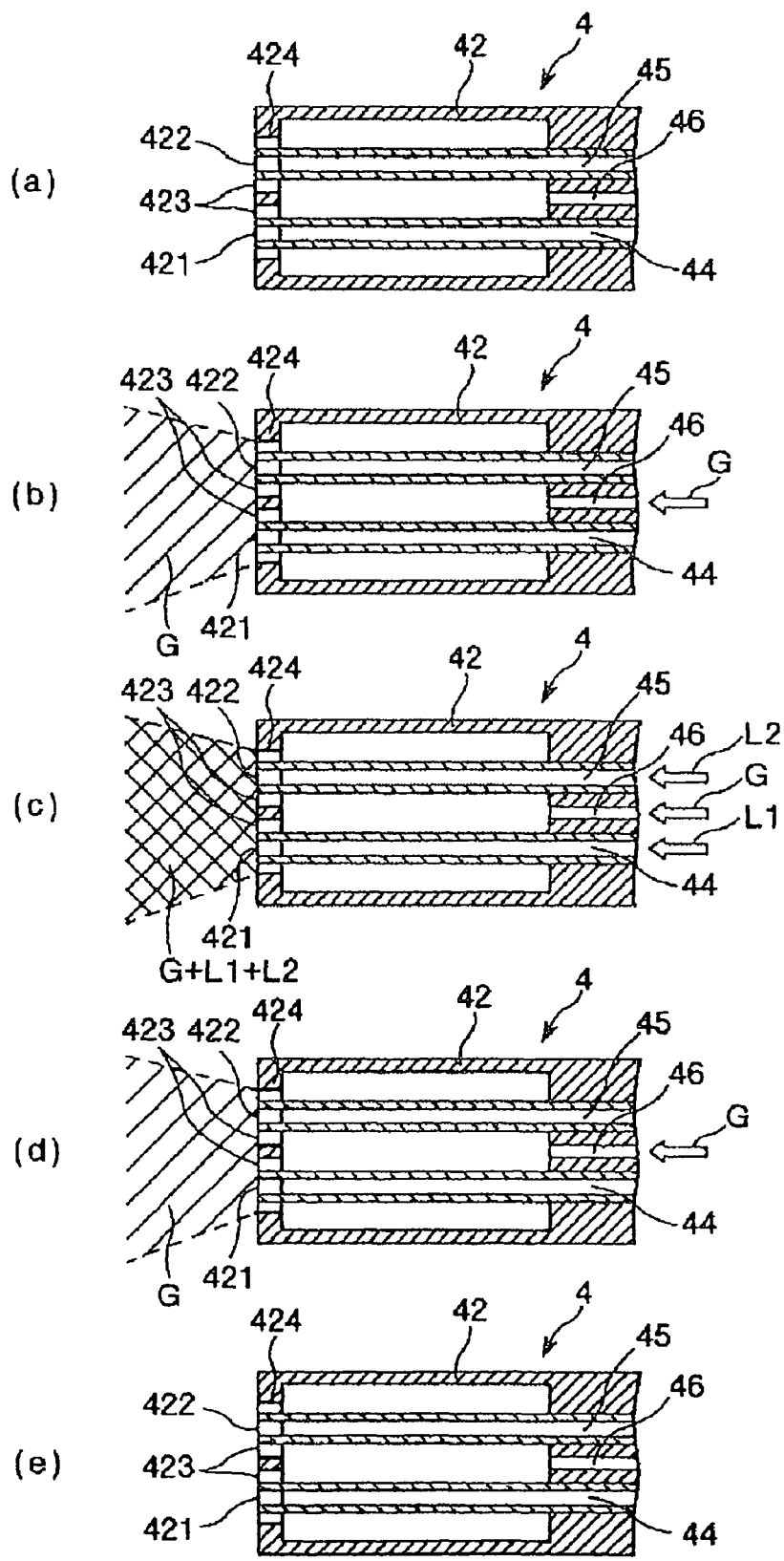
FIGS. 5A-5E are longitudinal cross-sectional views of the distal end part of the nozzle in the applicator shown in FIG. 1 illustrating different operational modes.

As shown in FIGS. 3 and 4, the opening and closing means 9 comprises a first connection part 91 connected to the first tube 101, a second connection part 92 connected to the second tube 102, and a closable valve part (valve) 93 stored in the first connection part 91.

The first connection part 91 is in the shape of a tube. A storage part 912 is provided in the bore of the first connection part 91 on the downstream side. The valve part 93 is stored in the storage part 912. Further, a reduced diameter part 913 is provided in the bore of the first connection part 91. The reduced diameter part 913 is reduced in diameter relative to the inner diameter on the upstream side of the storage part 93.

A step part 911 is provided at the boundary between the reduced diameter part 913 and the storage part 912. In the illustrated embodiment, the step part 911 exhibits a sharp change in inner diameter.

The second connection part 92 is tubular in shape. As described above, the second connection part 92 is connected to the pressing part 82 of the operation part 8. The bottom part 921 of the second connection part 92 is supported by a sealing member 94 of the valve part 93. Thus, the second connection part 92 is set on the downstream side of the first connection part 91 via the sealing member 94. The second connection part 92 is movably displaceable between a first posture in which it's axis is aligned with (coaxial) the axis of the first connection part 91 (the state shown in FIG. 3) and a second posture in which the axis of the second connection part 92 is tilted (canted) relative to the axis of the first connection part 91 in the direction of the arrow C in FIG. 4 (direction of operation) of the pressing part 82 (operation part 8) with the bottom part 921 as the fulcrum (the state shown in FIG. 4). Thus, in the FIG. 4 state, the axis of the first connection part 92 and the axis of the second connection part 91 are no longer aligned or coaxial with each other.

The valve part 93 includes the sealing member 94 formed of an elastic material, a flange part 95 situated on the upstream side of the sealing member 94, and an urging part 96 urging the flange part 95 toward the sealing member 94.

The sealing member 94 is in the shape of a ring (annular in form). The inner circumferential part 941 of the sealing member 94 is in close contact with the outer circumferential part 922 of the bottom part 921 of the second connection part 92. The outer circumferential part 942 of the sealing member 94 is in close contact with the inner circumferential part 914 of the storage part 912 of the first connection part 91. With such a sealing part 94, the first connection part 91 and the second connection part 92 are connected in an air-tight manner via the sealing member 94.

The flange part 95 has an outer diameter larger than the outer diameter of the second connection part 92. The flange part 95 is disposed in opposing relation to the bottom side of the second connection part 92 via a gap 97.

In this illustrated embodiment, the urging part 96 is in the form of a compressed spring. The spring s, in a compressed state, in contact with the flange part 95 at its upper edge 961, and in contact with the step part 911 of the first connection part 91 at its bottom part 962. The flange part 95 is thus urged to the side of the sealing member 94 with reliability.

With this construction of the valve part 93, when the second connection part 92 is in the first posture, i.e., when an external force is not applied to the second connection part 92, the flange part 95 is urged by the urging part 96 into air-tightly contact with the sealing member 94 as shown in FIG. 3. As a result, the valve part 93 is in a closed state.

When a pressing force acts on the second connection part 92 in the direction of the arrow C by the application of a force to the pressing part 82 of the operation unit 8, the second connection part 92 is displaced from the first posture to the second posture. The flange part 95 is thus displaced against the urging force of the urging part 96. As a result, a portion (or the entirety) of the peripheral part 951 of the flange part 95 is separated from the sealing member 94. This results in the formation of a gap 98 between the flange part 95 and the sealing member 94 as illustrated in FIG. 4. As a result, the gas G flows from the first connection part 91 into the second connection part 92 via the gap 98. Namely, the valve part 93 is placed in an opened state.

With the opening and closing means 9 having the foregoing construction, the valve part 93 can be reliably opened/closed in synchronization with the pressing operation by the operation part 8. As a result, when the valve part 93 is in a closed state, the flow of the gas G from the cylinder 300 to the nozzle 4 can be shut off in a relatively reliable manner. When the valve part 93 is in an opened state, the flow of the gas G is permitted with good reliability.

The materials forming the first connection part 91, the second connection part 92, the flange part 95, and the urging part 96 are not limited to specific materials. However, by way of example, various metal materials and various plastics may be used alone or in combination.

Though the materials forming the sealing member 94 are also not limited to specific materials, examples include various rubber materials such as natural rubber, butyl rubber, isoprene rubber, butadiene rubber, styrene-butadiene rubber, and silicone rubber.

The operation of the applicator is described below in which the applicator 1 is in a usable state, i.e., a state in which the first syringe 2 filled with the first liquid L1 is mounted in the applicator and the second syringe 3 filled with the second liquid L2 is mounted in the applicator.

The first syringe 2 and the second syringe 3 are filled with the first liquid L1 and the second liquid L2 respectively, each in an amount necessary (enough) to be applied onto the affected part. Also, the valve 301 is in an opened state, which allows the gas G to be supplied to the applicator 1 from the cylinder.

The applicator 1 is constructed so that the force for causing the gap 98 to form between the sealing member 94 and the flange part 95 against the force of the urging part 96 (urging force of the spring) that presses the flange part 95 against the sealing member 94, i.e., the pressing force in the direction of the arrow C to tilt the second connection part 92 from the first posture to the second posture, is set to be larger than the force to move the pusher 26 of the first syringe 2 and the pusher 26 of the second syringe 3 in the direction of the distal end. Such a setting can be accomplished in the following manner. For example, various conditions such as the spring constant of the urging part 96, the viscosity of each liquid, and the inner diameter of each outer tube 21 can be appropriately set.

Using the applicator 1, first, an index finger for example is rested on the finger rest part 751 of the applicator main body 7, a middle finger is rested on the finger rest part 752, and a thumb is rested on the pressing part 82 of the operation part 8. At this step generally shown in FIG. 5A, the gas G, the first liquid L1, and the second liquid L2 are not discharged from the nozzle 4.

Then, when the pressing part 82 is pressed and operated with a thumb in this state, the second connection part 92 is tilted. As a result, the gap 98 results between the sealing member 94 and the flange part 95. Thus, the gas G passes through the gap 98 and is able to flow downstream past the valve 93 as shown in FIG. 4. As a result, the gas G is ejected from each of the plural third discharge ports 423 of the nozzle 4.

Further, the pressing part 82 is pressed. Then, the second connection part 92 is tilted to its maximum extent or limit, so that the pressing force from the thumb is transferred to the connection part 81 via the pressing part 82. As a result, the connection part 81 starts to move. Accordingly, the first liquid L1 is pushed out from the first syringe 2, and the second liquid L2 is also pushed out from the second syringe 3. The pushed first liquid L1 passes through the first flow path 44 of the nozzle 4, and is ejected from the first discharge port 421 as generally shown in FIG. 5C. The second liquid L2 passes through the second flow path 45 of the nozzle 4, and is ejected from the second discharge port 422 roughly in the same manner as the first liquid L1 as generally shown in FIG. 5C.

The ejected first liquid L1 and second liquid L2 are respectively atomized by the action of the gas G as described above, and mutually mixed to be applied onto the affected part.

Each pusher 26 is fully pushed by the pressing operation of the operation part 8. Namely, when the movement of each pusher 26 stops, the first liquid L1 and the second liquid L2 respectively stop being ejected as shown in FIG. 5D. At this step, the gas G is still being ejected.

Thereafter, when the thumb which has pressed the pressing part 82 is removed from the pressing part 82, the pressing force against the second connection part 92 is released. Thus, the second connection part 92 returns to the first posture. As a result, the gap 98 between the sealing member 94 and the flange part 95 disappears. Namely, the sealing member 94 and the entire circumference of the peripheral part 951 of the flange part 95 come in close contact with each other as illustrated in FIG. 3. As a result, the gas G stops being ejected from each of the third discharge ports 423 as shown in FIG. 5E.

In this manner, with the applicator 1, it is possible to relatively optimally set the timing of supply/stopping of supply of the gas G with respect to the nozzle 4 when the first liquid L1 and the second liquid L2 are discharged/stopped from being discharged from the nozzle 4. In other words, the applicator 1 is configured such that the gas G is discharged from the nozzle 4 before the first liquid L1 and the second liquid L2 with relative ease and with reliability.

This can prevent the first liquid L1 and the second liquid L2 from being applied onto the affected part without being mixed with the gas G. Further, by the previously ejected gas G, the first liquid L1 and the second liquid L2 are respectively ejected in an atomized form with reliability. As a result, these liquids are mixed with each other in a reliable manner.

Further, the applicator 1 is configured such that the gas G stops being ejected later than the first liquid L1 and the second liquid L2. That is, the ejection of the first and second liquids stops before ejection of the gas G stops. As a result, when the ejection of the liquids stops, but liquid remains (is deposited) on the respective discharge port, the gas G can blow away these remaining liquid deposits. As a result, it is possible to prevent the disadvantage (e.g., clogging of each discharge port due to coagulation) caused by the reaction between the first liquid and the second liquid in the vicinity of each discharge port.

FIG. 6 is a longitudinal cross sectional view of the opening and closing means in an applicator according to a second embodiment.

The following description of the second embodiment of the applicator will primarily focus on a description of aspects and features of the applicator that differ from those associated with the first embodiment. Features in the second embodiment of the applicator that are the same as those in the first embodiment are identified by a common reference numeral, and a description of such features will not be repeated.

This second embodiment of the applicator is the same as the first embodiment except that the applicator further has an urging force adjusting means.

The applicator 1A shown in FIG. 6 further includes an urging force adjusting means 5 for adjusting the urging force of the urging part (spring) 96. The particular construction of the urging force adjusting means 5 is not limited. However, in this embodiment, the urging force adjusting means 5 is in the form of an annular member or ring member (spacer) 51 in the shape of a ring.

The outer diameter of the ring member 51 is roughly the same as the outer diameter of the urging part 96. The ring member 51 is stored in the storage part 912 of the first connection part 91, and is situated between the end (bottom) part 962 of the urging part 96 and the step part 911. As a result, it is possible to compress the urging part 96 more than the urging part 96 of the first embodiment. Accordingly, it is possible to adjust the urging force, i.e., to increase the urging force.

The force for moving the pusher 26 of the first syringe 2 and the pusher 26 of the second syringe 3 in the direction of the distal end (hereinafter referred to as a "moving force") varies according to, for example, the viscosities of the first liquid L1 and the second liquid L2, and the inner diameter of each outer tube 21.

For example, when the first liquid L1 filled in the first syringe 2 is a liquid having a relatively large (high) viscosity, the moving force may be larger than the pressing force in the direction of the arrow C for tilting the second connection part 92 from the first posture to the second posture. For this reason, when the pressing part 82 is pressed with a certain force, the valve part 93 is moved to the opened state, but the pushers 26 may not be moved to eject the liquids L1, L2. Thus, only the gas G continues being ejected. Accordingly, the first liquid L1 and the second liquid L2 may not be pressed out (may not be ejected).

When the first liquid L1 in the first syringe 2 is one having a relatively small viscosity, the moving force may be extremely smaller than the pressing force in the direction of the arrow C for tilting the second connection part 92 from the first posture to the second posture. For this reason, even when the pressing part 82 is pressed, the pushers 26 are first moved (i.e., the pressers 26 move before the valve 93 is opened). Thus, only the first liquid L1 and the second liquid L2 are ejected. Thus, the valve part 93 is kept in a closed state, so that the gas G may not be ejected.

By outfitting the applicator 1A with the urging force adjusting means 5, it is possible to address various factors which might otherwise affect the ejection of the liquids L1, L2 or the gas G. As a result, for example, as described above, even when the first liquid L1 is one having a relatively large (high) viscosity, by increasing the urging force of the urging part 96, the pressing force in the direction of the arrow C for tilting the second connection part 92 from the first posture to the second posture can be reliably set larger than the moving force. As a result, the gas G is ejected from the nozzle 4 before the first liquid and the second liquid L1, L2. Namely, it is possible to set the optimum ejection timing of the nozzle 4. For example, it is possible to begin blowing out the first liquid L1 and the second liquid L2 after 0.2 second following the beginning of ejection of the gas G.

The material forming the ring member 51 is not particularly limited. Examples of suitable materials include various metal materials and various plastics, used alone or in combination.

Also, the urging force adjusting means 5 is not limited to the ring member 51. Indeed, other alternatives are possible. For example, the portion defining the storage part 912 of the first connection part 91 is formed of a first member situated on the upstream side, and a second member situated on the downstream side relative to the first member. These members are bonded by screwing together. This enables the first member and the second member to move closer to each other, or away from each other. Accordingly, it is possible to adjust the distance between the flange part and the step part. As a result, effects similar to those associated with the ring member 51 can be realized.

The applicator here has been described by way of the embodiments shown in the drawing figures. However, the applicator is not limited in this regard. Each part forming the applicator can be replaced with one having a given configuration capable of exerting the same or similar function. Further, a given structure may be added.

Further, the applicator is configured such that the first liquid which has passed through the reduced diameter part of the first syringe and the second liquid which has passed through the reduced diameter part of the second syringe are ejected from the nozzle at roughly the same time. However, the present invention is not limited in that regard. For example, the applicator can also be configured such that one of these two liquids is ejected before the other.

The applicator disclosed here is used with a first syringe and a second syringe, with both syringes comprising a syringe outer tube having an opening part formed in a protruding manner at the distal end part, a gasket in the syringe outer tube, and a pusher for moving and operating the gasket along the longitudinal direction of the syringe outer tube. The syringes are each filled with respective and different liquids, such that the liquid is in a space in the syringe outer tube between the gasket and the opening part. The applicator includes an applicator main body for arranging and fixing the first syringe and the second syringe, a gas flow path connected to a gas supply means for supplying a gas and through which a gas from the gas supply means passes, and a nozzle for discharging therethrough the gas which has passed through the gas flow path, the liquid which has passed though the opening part of the first syringe, and the liquid which has passed though the opening part of the second syringe. In addition an operation part is provided for pressing and operating the pusher of the first syringe and the pusher of the second syringe in the direction of the distal end. An opening and closing means is provided in the operation part for shutting off/opening the gas flow path. The opening and closing means operates to open the gas flow path in synchronization with the pressing operation by the operation part. For this reason, it is possible to carry out the supply/stoppage of supply of the gas with respect to a nozzle with relative ease and reliability when a liquid is discharged/stopped from being discharged from the nozzle.

The principles, embodiments and modes of operation of the applicator here have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An applicator comprising:
   an applicator main body having a first syringe receiving region and a second syringe receiving region;
   a first syringe positioned in the first syringe receiving region, the first syringe comprising an outer tube possessing an opening at its distal end and a pusher movably positioned in the outer tube, a rear end of the pusher extending outside the outer tube, and a first liquid in the outer tube of the first syringe, the pusher being movable in a longitudinal direction of the applicator main body toward a distal end of the outer tube;
   a second syringe positioned in the second syringe receiving region, the second syringe comprising an outer tube possessing an opening at its distal end and a pusher movably positioned in the outer tube, a rear end of the pusher of the second syringe extending outside the outer tube of the second syringe, and a second liquid in the outer tube of the second syringe, the second liquid being different from the first liquid, the pusher of the second syringe being movable in the longitudinal direction of the applicator main body toward a distal end of the outer tube of the second syringe;
   a gas supply;
   a gas flow path connected to the gas supply and through which gas from the gas supply passes;
   the gas flow path being connected to a nozzle through which is discharged the gas which has passed through the gas flow path, the first liquid which has passed though the opening of the outer tube of the first syringe, and the second liquid which has passed though the opening of the outer tube of the second syringe;
   a valve positioned along the gas flow path to permit flow of the gas to the nozzle when the valve is in an open state and preventing the flow of the gas to the nozzle when the valve is in a closed state; and
   a pressing part operable by a user in the longitudinal direction of the applicator main body toward the distal end of the outer tubes of the first and second syringes, said pressing part being directly operatively connected to the valve and the pushers of the first and second syringes, the pressing part being operable by the user to position the valve in the open state and move the pushers toward the distal end of the respective outer tubes to discharge the gas and the first and second liquids out of the nozzle, with the first and second liquids being mixed exteriorly of the nozzle.

2. The applicator according to claim 1, wherein a rear end of the outer tube of the first syringe and the second syringe comprises a radially outwardly extending flange, the applicator main body comprising a grooved region receiving the flange of the outer tube of the first syringe and the flange of the outer tube of the second syringe so that the outer tube of the first and second syringes are fixed in position relative to the applicator main body.

3. The applicator according to claim 1, wherein the rear end of the pusher of the first syringe and the rear end of the pusher of the second syringe each comprise a radially outwardly extending flange, the valve being movable together with a connection part that includes a grooved region, the flange at the rear end of the pusher of the first syringe and the flange at the rear end of the pusher of the second syringe being positioned in the grooved region of the connection part.

4. The applicator according to claim 1, wherein the valve comprises a sealing member formed of elastic material, a flange part positioned upstream of the sealing member relative to a direction of gas flow, and a spring urging the flange part toward the sealing member.

5. The applicator according to claim 1, wherein the nozzle comprises a first through hole connected to the opening at the distal end of the outer tube of the first syringe, a second through hole connected to the opening at the distal end of the outer tube of the second syringe, and a plurality of third through holes connected to the gas flow path.

6. The applicator according to claim 1, wherein the first liquid and the second liquid mixed together exterior of the nozzle form an adhesion preventive material of a biological tissue.

7. An applicator to be used with a first syringe and a second syringe, the first syringe and the second syringe each comprising a syringe outer tube having an opening part protruding from a distal end part of the syringe outer tube, a gasket in the syringe outer tube, and a pusher for moving the gasket along a longitudinal direction of the syringe outer tube, and each syringe outer tube being filled with a liquid between the opening part and the gasket, the applicator comprising:

an applicator main body for receiving the first syringe and the second syringe;

a gas flow path adapted to be connected to a gas supply for supplying a gas, and through which a gas from the gas supply means passes;

a nozzle through which is discharged the gas which has passed through the gas flow path, the first liquid which has passed though the opening of the first syringe, and the liquid which has passed though the opening part of the second syringe;

an operation part adapted to be pressed by a user in the longitudinal direction of the syringe outer tube and in a distal end direction to directly operate the pusher of the first syringe and the pusher of the second syringe in the distal end direction;

opening and closing means disposed in the operation part for shutting off/opening the gas flow path; and the opening and closing means being operable to open the gas flow path in synchronization with the pressing operation by the operation part.

8. The applicator according to claim 7, wherein the opening and closing means is positioned midway in the gas flow path, and is formed of a closable valve mechanism.

9. The applicator according to claim 8, wherein the valve mechanism comprises a tube-shaped first connection part having an axis and connected to an upstream side of the gas flow path, a second tube-shaped connection part connected to a downstream side of the gas flow path and having an axis, and a valve part, the second connection part being movable in response to operation of the operation part in an operating direction between a first posture in which the axis of the second connection part and the axis of the first connection part are coaxial, and a second posture in which the axis of the second connection part is tilted in the operation direction with respect to the axis of the first connection part, the valve part being closed when the second connection part is in the first posture, and being opened when the second connection part is in the second posture.

10. The applicator according to claim 9, wherein the valve part comprises a sealing member formed of an elastic material connecting an inner circumferential part of the first connection part and an outer circumferential part of the second connection part in an air-tight manner, a flange part possessing a diameter larger than an outer diameter of the second connection part on the upstream side of the gas flow path of the second connection part, and an urging part urging the flange part to the side of the sealing member, the flange part being urged by the urging part into air-tight contact with the sealing member when the second connection part is in the first posture, and being displaced against the urging force of the urging part to cause a gap between the flange part and the sealing member when the second connection part is in the second posture.

11. The applicator according to claim 10, wherein the operation part and the opening and closing means are constructed such that the gas which has passed through the gas flow path is discharged from the nozzle at the same time as, or before, the liquid in at least one of the syringes is ejected from the nozzle.

12. The applicator according to claim 11, wherein a force required to cause the gap between the sealing member and the flange part is larger than the force for moving the pusher of the first syringe and the pusher of the second syringe in the distal end direction.

13. The applicator according to claim 12, further comprising an urging force adjusting means for adjusting the urging force of the urging part.

14. The applicator according to claim 7, wherein the operation part comprises a connection part connecting proximal end parts of the pushers of the first syringe and the second syringe with each other, and a pressing part to be pressed by a user.

15. The applicator according to claim 14, wherein the applicator main body comprises a finger rest part on which a finger of a user's hand is rested, with a thumb of the user's hand resting on the pressing part.

16. The applicator according to claim 7, wherein the applicator main body comprises a first fitting part with which the opening parts of the first syringe and the second syringe are each adapted to be fitted, and a second fitting part with which proximal end parts of the first syringe and the second syringe are each fitted, the second fitting part being proximally disposed relative to the first fitting part.

17. The applicator according to claim 7, wherein the nozzle comprises a first discharge port through which is to be discharged the liquid of the first syringe, a first flow path along which is to be fed the liquid from the first syringe to the first discharge port, a second discharge port through which is to be discharged the liquid of the second syringe, a second flow path along which is to be fed the liquid from the second syringe to the second discharge port, gas discharge ports concentrically positioned circumferentially outwardly of the first discharge port and the second discharge port, and through which is to be discharged the gas from the gas supply, and a third flow path along which is to be fed the gas from the gas supply to the gas discharge ports.

18. A method of applying a composition to a region through use of an applicator comprising a nozzle connected to a first syringe containing a first liquid, a second syringe containing a second liquid different from the first liquid, and a gas flow path connected to a gas supply, comprising:

pressing a pressing portion of the applicator in a longitudinal direction of the applicator toward a distal end of the first and second syringes to open a valve positioned along the gas flow path to permit gas from the gas supply to flow along the gas flow path to the nozzle, with the gas being discharged through the nozzle; and the pressing of the pressing portion also directly causing the first liquid in the first syringe to be ejected from the first syringe to the nozzle, with the first liquid being discharged through the nozzle and atomized exterior of the nozzle by the gas discharged through the nozzle to produce an atomized first liquid;

the pressing of the pressing portion also directly causing the second liquid in the second syringe to be ejected from the second syringe to the nozzle, with the second liquid being discharged through the nozzle and atomized exterior of the nozzle by the gas discharged through the nozzle to produce an atomized second liquid; and the atomized first and second liquids mixing together exterior of the nozzle to produce a composition applied to the region.

19. The method according to claim 18, wherein the composition is an adhesion preventive material and the region is a region of a living body.

20. The method according to claim 18, wherein the composition is a biological tissue adhesive and the region is a region of a living body.

21. The applicator according to claim 1, wherein said valve includes a first connection part, an openable/closable valve part disposed with said first connection part, and a second connection part operatively connecting said openable/closable valve part to said pressing part, said pressing part being operable by a user in a direction substantially perpendicular to an axis of the second connection part, said second connection part being axially aligned with said first connection part when the valve is in the closed state and the axis of said second connection part being tilted relative to an axis of said first connection part when the valve is in the open state.

22. The method according to claim 18, wherein the valve includes a first connection part, an openable/closable valve part disposed with the first connection part, and a second connection part operatively connecting the openable/closable valve part to the pressing portion, and wherein said pressing of the pressing portion in a direction substantially perpendicular to an axis of the second connection part causes the axis of the second connection part to tilt relative to an axis of the first connection part, thereby opening the openable/closable valve part and permitting gas from the gas supply to flow along the gas flow path.

* * * * *